United States Patent [19]

Nelson

[11] 4,345,301
[45] Aug. 17, 1982

[54] CAPACITIVE HUMIDITY TRANSDUCER

[75] Inventor: Marvin D. Nelson, St. Louis Park, Minn.

[73] Assignee: Honeywell Inc., Minneapolis, Minn.

[21] Appl. No.: 237,007

[22] Filed: Feb. 23, 1981

[51] Int. Cl.³ .......................... H05K 1/18; H01G 7/00
[52] U.S. Cl. .................................. 361/400; 73/336.5; 361/286; 361/405
[58] Field of Search ............... 361/286, 303, 400, 405; 73/336.5

[56] References Cited

U.S. PATENT DOCUMENTS

| 1,708,073 | 4/1929 | Allen | 361/286 X |
| 1,899,176 | 2/1933 | Bailey | 361/303 X |
| 4,164,868 | 8/1979 | Suntola | |
| 4,305,112 | 12/1981 | Heywang | 361/286 |

FOREIGN PATENT DOCUMENTS 1197561 7/1965 Fed. Rep. of Germany ...... 361/303

OTHER PUBLICATIONS

Channon A thick, "Film Humidity Sensor", in Conf. on Hybrid Microelectronics, Loughborough, Leis, England, 9/9/75, pp. 57–62.
Thoma, "A Capacitance Humidity Sensing Transducer", in IEEE Transactions on Components, Hybrids & Manufacturing Technology, vol. CHMT-2, #3, 9/79, pp. 321–323.

Primary Examiner—Elliot A. Goldberg
Attorney, Agent, or Firm—Lockwood D. Burton; Mitchell J. Halista

[57] ABSTRACT

A capacitive humidity transducer having an electrically non-conductive dielectric base carrying a pair of electrically conductive coatings deposited directly on opposite respective sides of the non-conductive base to form parallel capacitor plates. The conductive coatings are each arranged in a configuration of a plurality of side-by-side forked legs with the legs of the electrically conductive elements being positioned in a facing relationship. One end of each of the electrically conductive coatings is provided with electrical connectors for attaching the transducer to respective electrically conductive circuits which may be on a printed circuit board. The dielectric base is arranged to be hygroscopic whereby atmospheric humidity provides a corresponding variation in the dielectric constant of the base to affect the capacitance of the transducer.

4 Claims, 3 Drawing Figures

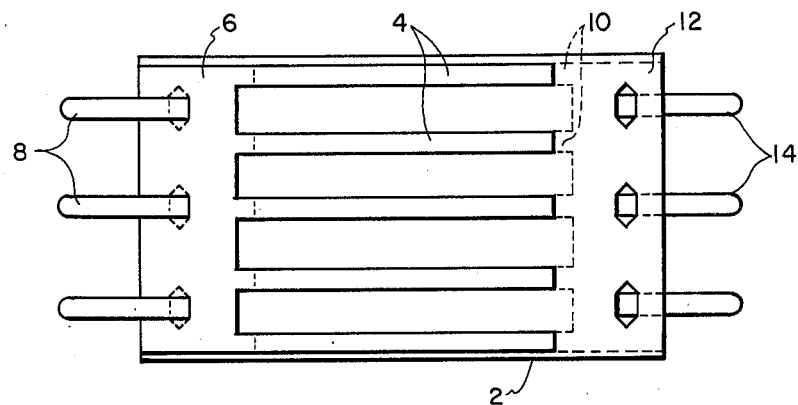
F I G. 1
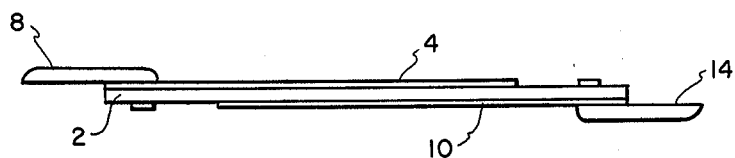
F I G. 2
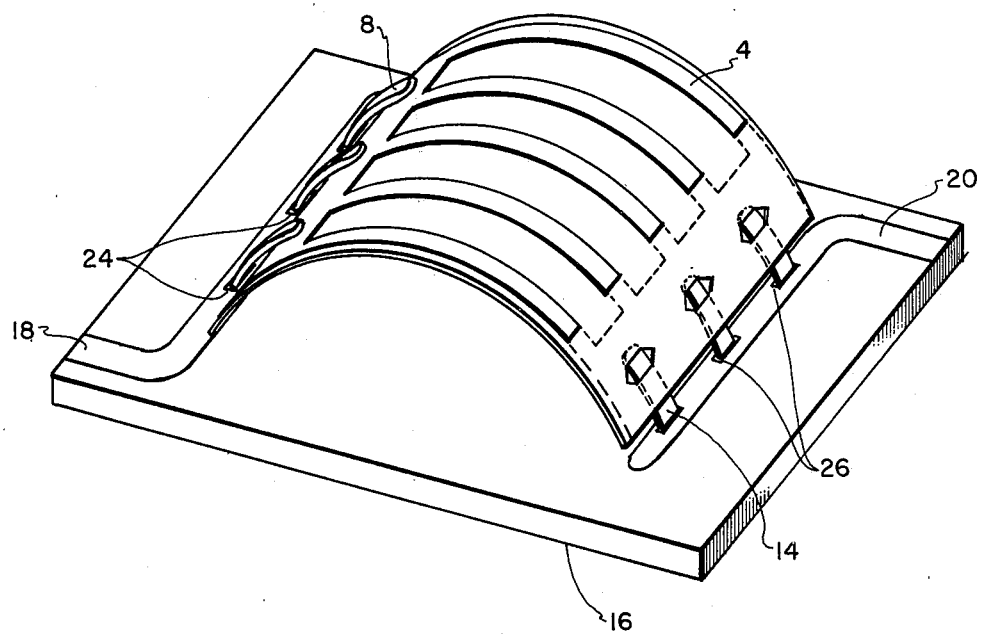
F I G. 3

CAPACITIVE HUMIDITY TRANSDUCER

BACKGROUND OF THE INVENTION

1. Field Of The Invention

The present invention relates to humidity transducers. More specifically, the present invention is directed to a capacitive humidity transducer.

2. Description Of The Prior Art

The desirability of providing an indication of a humidity in the atmosphere is well-known in various applications. The prior art has generally taken two different approaches. One of these approaches involves using a resistor which has variations in resistance in accordance with corresponding changes in environmental humidity. The second approach is directed to a capacitive transducer. A typical prior art capacitive humidity transducer is shown in U.S. Pat. No. 4,164,868. Such a conventional capacitive humidity transducer is significantly limited in its response time to change in atmospheric humidity by having a complex supporting dielectric structure as well as large are a solid electrically conductive coatings which effectively impede the absorption and adsorption of water molecules into the dielectric material. Accordingly, it would be desirable to provide a capacitive humidity transducer which had a significantly improved humidity variation response time over the aforesaid prior art capacitive humidity transducers.

SUMMARY OF THE INVENTION

An object of the present invention is to provide an improved capacitive humidity transducer having a short response time to changes in atmospheric humidity.

In accomplishing this and other objects, there has been provided, a capacitive humidity transducer having a first and second electrically conductive coating deposited on opposite sides of a hygroscopic dielectric support member. The electrically conductive coatings are each configured as a common conductive strip having a plurality of side-by-side forked extensions thereof in a mutually facing relationship through the support member.

BRIEF DESCRIPTION OF THE DRAWINGS

A better understanding of the present invention may be had when the following detailed description is read in connection with the accompanying drawings, in which:

FIG. 1 is a top view of an example of a capacitive humidity transducer embodying the present invention, FIG. 2 is a side view of the transducer shown in FIG. 1 and FIG. 3 is a perspective view of the capacitive humidity transducer of FIGS. 1 and 2 mounted on a printed circuit board.

DESCRIPTION OF THE PREFERRED EMBODIMENT

Referring to FIG. 1 in more detail, there is shown a capacitive humidity transducer embodying an example of the present invention and utilizing a dielectric base member of a hygroscopic material which is responsive to atmospheric humidity, e.g., polyimide film. The base member 2 has deposited thereon a first plurality of electrically conductive elements 4 arranged as side-by-side forked extensions of a common electrically conductive strip 6. The electrically conductive strip 6 is, in turn, connected to electrical connecting pins 8 attached thereto. A second plurality of side-by-side forked leg elements 10 are arranged on the opposite side of the base member 2 in a mutually facing relationship with the first forked elements 4. The second elements 10 are extensions of a common electrically conductive strip 12. The conductive strip 12, in turn, is connected to electrically conductive pins 14. The first and second electrically conductive deposits can be of copper having a thickness of approximately five thousands of an inch (0.005"). A side view of this transducer structure is shown in FIG. 2. The capacitance of the transducer is measured between the electrically conductive deposits defining the extensions 4, 10. Since these extensions 4, 10 are rigidly attached to the base 2, the transducer of the present invention has a high mechanical strength which promotes accuracy and repeatability of performance.

In FIG. 3, there is shown an example of a mounting of the capacitive humidity transducer shown in FIGS. 1a and 2 on a printed circuit board 16. The printed circuit board 16 has a first electrically conductive circuit 18 deposited thereon and a second electrically conductive circuit 20 spaced from the first electrically conductive circuit 18 by a distance less than the length of the base member 2 of the transducer, e.g., the spacing of the pins 8 and 14. The electrically conductive pins 8 and 14 on the transducer are arranged to fit into holes 24, 26 in the printed circuit board circuits 18 and 22 and are electrically attached, e.g., soldered, thereto. The spacing of the circuits 18 and 20 is effective to bow the base member 2 away from the board 16 to provide a degree of rigidity to the capacitive humidity transducer and to minimize stray capacitance. The bifurcated arrangement of the electrically conductive legs 4 and 10 is effective to expose a large area of the dielectric member 2 between the legs 4 and 10 to the atmospheric humidity to significantly accelerate the response of the dielectric member 2 to changes in atmospheric humidity.

Accordingly, it may be seen, that there has been provided, in accordance with the present invention, an improved capacitive humidity transducer having a fast response time to changes in atmospheric humidity.

The embodiments of the invention in which an exclusive property or privilege is claimed are defined as follows:

1. A capacitive humidity transducer comprising
  an electrically non-conductive base member of a hygroscopic material,
  a first electrically conductive coating on said base member arranged as a plurality of side-by-side extensions joined at one end to a common electrically conductive strip,
  a second electrically conductive coating on said base member arranged as a plurality of side-by-side extensions joined at one end to a common electrically conductive strip and located on the opposite side of said base member from said first coating with said extensions of said first and second coatings being arranged in a facing relationship, said base member and said extensions forming a capacitor affected by atmospheric humidity as a result of the hygroscopic activity of said base member,
  a first electrical connector for said first coating,
  a second electrical connector for said second coating and a printed circuit board having a first circuit thereon receiving said first connector and a second circuit thereon receiving said second connector, said first and second circuits being spaced closer together than the spacing of said first and second connectors.

2. A capacitive humidity transducer as set forth in claim 1 wherein said first and second coatings are copper.

3. A capacitive humidity transducer as set forth in claim 2 wherein said base member is a polyimide film.

4. A capacitive humidity transducer as set forth in claim 1 wherein said extensions of said first and second coatings are each at least three in number.

* * * * *